US007026520B1

United States Patent
Mukhopadhyay et al.

(10) Patent No.: US 7,026,520 B1
(45) Date of Patent: Apr. 11, 2006

(54) CATALYTIC CONVERSION OF HYDROFLUOROALKANOL TO HYDROFLUOROALKENE

(75) Inventors: Sudip Mukhopadhyay, Buffalo, NY (US); HsuehSung Tung, Getzville, NY (US); Haridasan K. Nair, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/006,922

(22) Filed: Dec. 8, 2004

(51) Int. Cl.
*C07C 17/00* (2006.01)
*C07C 17/08* (2006.01)
*C07C 21/18* (2006.01)
*C07C 23/00* (2006.01)
*C07C 25/13* (2006.01)

(52) U.S. Cl. .................. 570/123; 570/140; 570/142
(58) Field of Classification Search ................ 570/123, 570/140, 142
See application file for complete search history.

(56) References Cited

U.S. PATENT DOCUMENTS

| 2,931,840 | A | | 4/1960 | Marquis | |
|---|---|---|---|---|---|
| 4,900,874 | A | * | 2/1990 | Ihara et al. ................ | 570/142 |

FOREIGN PATENT DOCUMENTS

| EP | 328148 | 8/1989 |
|---|---|---|
| JP | 06072925 | 3/1994 |

* cited by examiner

*Primary Examiner*—Johann Richter
*Assistant Examiner*—Chukwuma Nwaonicha
(74) *Attorney, Agent, or Firm*—Colleen D. Szuch

(57) ABSTRACT

Methane is used as the selective dehydrating agent for the production of 2,3,3,3-tetrafluoro-1-propene (R1234yf) from 2,2,3,3,3-pentafluoro-1-propanol. Supported transition metal catalysts are prepared and used for this reaction with high activity. Almost 58% selectivity to R1234yf is obtained at an alcohol conversion level of 60% using unsupported Ni-mesh as the catalyst. Pd and Pt show almost similar level of conversion; however, the selectivity to the desired product is low. The activity of the metal catalyst was found to be a function of the type of support material, activated carbon showing better activity than alumina. Different important process parameters such as temperature, pressure, and contact time are studied to optimize the process. High pressure and temperature are deleterious to the rate of 1234yf formation; yet, the highest yield to 1234yf is obtained while performing a reaction at 494° C. with a contact time of 23 sec.

23 Claims, No Drawings

CATALYTIC CONVERSION OF HYDROFLUOROALKANOL TO HYDROFLUOROALKENE

BACKGROUND OF THE INVENTION

1. Field of the Invention

The present invention is a novel catalytic process for making hydrofluoroalkene from a hydrofluoroalkanol in high yield using a dehydrating agent and in the presence of a catalyst. More particularly, it relates to making $CF_3CF=CH_2$ from $CF_3CF_2CH_2OH$ in high-yield using methane as the reducing agent in the presence of a transition metal catalyst.

2. Discussion of the Background Art 2,3,3,3-tetrafluoro-1-propene (R1234yf), which is a probable candidate for low global warming potential refrigerant, has been synthesized by pyrolysis of methyl chloride and tetrafluoroethylene or chlorodifluoromethane. In a reaction, 55 cc./min. MeCl and 110 cc./min. $CHClF_2$ is passed through a Pt tube 6 mm.×24 in. heated to 800° C. The gaseous products are scrubbed free of HCl and dried to yield only a small amount (14.8 mole-%) of 2,3,3,3-tetrafluoropropene. This process is a low yield process and because of the conversion of pentafluoropropanol obtained in our hand is as high as 100%, almost 90% of the starting material is lost to unimportant byproducts including a sizeable amount of carbon black.

On the other hand, 2,3,3,3-pentafluoro-1-propanol, which is generally synthesized by the reaction of tetrafluoroethylene, formaldehyde, and HF in the presence of TiF4 as the catalyst and limonene as the polymer inhibitor, can serve as a starting material to synthesize 2,3,3,3-pentafluoro-1-propene (R1234yf). It has been shown previously that fluorine-containing olefins $CH_2=CFRf[Rf=(per)haloalkyl group)]$ are prepared at low cost and low toxic waste generation by high-temperature dehalohydrogenation and dehydration of fluoroalcohols such as $HOCH_2CF_2Rf$ in the presence of $H_2$ gas. Feeding an activated C-packed tube at 500° C. with a 1:3 (mol/mol) mixed gas of $HOCH_2(CF_2)_4H$ and $H_2$ with a residence time of 4 sec yielded $CH_2:CF(CF_2)3H$ at monomer conversion 64% and selectivity 82%. This is a high-yield process; however, for a plant level production, the handling of $H_2$ at high temperature raises serious safety related questions.

Also, one needs to couple a $H_2$ plant on site with the 1234yf plant. This requires high installment cost. Thus, there is incentive to look for an alternative catalytic process scheme involving an alternative reducing agent instead of hydrogen.

The present invention also provides many additional advantages, which shall become apparent as described below.

SUMMARY OF THE INVENTION

The present invention involves the making of $CF_3CF=CH_2$ from $CF_3CF_2CH_2OH$ in high-yield using methane as the reducing agent in the presence of a transition metal catalyst.

Methane is used as the selective dehydrating agent for the production of 2,3,3,3-tetrafluoro-1-propene (R1234yf) from 2,2,3,3,3-pentafluoro-1-propanol. Supported transition metal catalysts are prepared and used for this reaction with high activity. Almost 58% selectivity to R1234yf is obtained at an alcohol conversion level of 60% using unsupported Ni-mesh as the catalyst. Pd and Pt show almost similar level of conversion; however, the selectivity to the desired product is low. The activity of the metal catalyst was found to be a function of the type of support material, activated carbon showing better activity than alumina. Different important process parameters such as temperature, pressure, and contact time are studied to optimize the process. High pressure and temperature are deleterious to the rate of 1234yf formation; yet, the highest yield to 1234yf is obtained while performing a reaction at 494° C. with a contact time of 23 sec.

Further objects, features and advantages of the present invention will be understood by reference to the following drawings and detailed description.

DETAILED DESCRIPTION OF THE PREFERRED EMBODIMENT

A process for producing a hydrofluoroalkene product which comprises: mixing a dehydrating agent with a hydrofluoroalkanol, thereby forming a gaseous mixture; and contacting a catalyst with the gaseous mixture, thereby forming the hydrofluoroalkene product.

The hydrofluoroalkanol is at least one selected from the group consisting of: fluoroalkanols having the general formula $RCH_2OH$ including, but not limited to, pentafluoropropanol, wherein R is selected from the group consisting of: $CF_3$, $CF_3CF_2$, $CF_3CF_2CF_2$, and $CF_3CF_2CF_2CF_2$. The pentafluoropropanol is preferably 2,2,3,3,3-pentafluoro-1-propanol.

The catalyst is preferably at least one transition metal selected from the group consisting of: Ni, Pd, and Pt. Preferably, the catalyst is a supported catalyst which comprises a transition metal and a support material. The support material is at least one selected from the group consisting of: activated carbon and γ-alumina.

The dehydrating agent is at least one gas selected from the group consisting of: methane, ethane, propane, butane, natural gas, alcohols, aldehydes, and carbon monoxide.

The mixing step takes place at a temperature in the range between about 65–80° C.

The process further comprises preheating the gaseous mixture prior to the contacting step. The preheating takes place at a temperature in the range between about 250 to about 450° C.

The contacting step preferably takes place at a temperature in the range between about 400 to about 700° C. The contacting step also preferably takes place for between about 20 to about 25 seconds.

The process further comprises the step of neutralizing any residual HF contained in the hydrofluoroalkene product, wherein the HF is neutralized by passing the hydrofluoroalkene product through a KOH solution.

The hydrofluoroalkene product comprised at least one hydrofluoro alkene selected from the group consisting of: 2,3,3,3-tetrafluoro-1-propene or any hydrofluoroalkene selected from the group consisting of compounds represented by the formula:

$$R_fCF=CH_2$$

wherein $R_f$ is selected from the group consisting of: $CF_3$, $CF_3CF_2$, and $CF_3CF_2CF_2$.

The gaseous mixture may further comprise at least one diluent inert gas selected from the group consisting of: nitrogen, helium, and argon.

The conversion of the hydrofluoroalkanol to hydrofluoroalkene is in the range between about 50 to about 100%.

The selectivity of hydrofluoroalkanol to hydrofluoroalkene is in the range between about 29 to about 100%.

The pressure during the contacting step is in the range between about 1 to about 100 psig.

EXAMPLE 1

The following example demonstrates the novel $CF_3CF=CH_2$ reaction process according to the present invention:

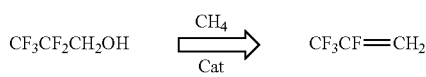

Scheme 1, Dehydration of Pentafluoropropanol in the presence of methane

Methane is used as a mild dehydrogenating agent to synthesize 1234yf from pentafluoropropanol (scheme 1). In a typical reaction, 40 sccm of $N_2$ and 20 sccm of methane were passed through a cylinder containing pentafluoropropanol at 65–80° C. to achieve a flow of pentafluoropropanol at 8 gm/hr (20 sccm). The gas mixtures were then passed through a preheater at 350° C. and then finally through a catalyst bed comprising of 100 cc of the active catalyst at 400–700° C. The effluent gas mixtures were passed through a 20% KOH solution to neutralize any HF formed during the reaction to KF and $H_2O$. The product mixture was analyzed and identified by GC and GCMS analysis.

The contact time was kept around 20–25 seconds depending on the reaction conditions. The catalysts used for this reaction were selected from transition metals including Ni, Pd, and Pt and the support materials were chosen from thermally stable materials such as activated carbon, carbon nanotubes, SBA-15, $SiO_2$, and γ-alumina.

EXAMPLE 2

Catalyst Preparation

In the catalyst preparation step, 1.5 to 2.0 gm of the metal (II) chloride precursor salts were dissolved in 100 cc methanol at 60° C. and then reduced to zero oxidation state by gradually adding stoichiometric amount of reducing agents such as potassium formate, hydrazine, or sodium borohydride in the form of an aqueous solution (10–15% wt/vol) in a semi-batch mode with an addition rate of 1–2 gm/hr. A 50 ml/min of $H_2$ was also used as the reducing agent by bubble through the precursor solution under atmospheric pressure at 60° C. After reduction of the metal salts, 100 cc of the support material was added under stirring to the solution and then mixed, concentrated, and dried in a vacuum oven at room temperature over a period of 80–100 hrs. The vacuum dried material was then taken in to a 1-inch monel tube reactor and further dried and calcined in the presence of anhydrous 50 sccm of $N_2$ at 350–550° C. The catalysts, thus prepared, are then finally reduced with a mixture of 10% $H_2$ in $N_2$ at 350° C. for 1 hr and then used as such for the above-mentioned reaction.

Results and Discussions

Table 1, #1–10 shows the results of the experiments using different catalysts under different conditions. It is observed that almost similar conversions were achieved with each one of the catalysts. However, the selectivity to 2,3,3,3-tetrafluoro-1-propene (1234yf) was found to be a function of the active catalyst component. With Ni-mesh, 58% selectivity to the product olefin was obtained; whereas, only 33% selectivity to the desired product was obtained using Pd/Alumina as the catalyst. The major byproducts were 1,1,1,2,2-pentafluoro-2-chloroethane (R115), Pentafluoroethane (R125), Trifluoromethane (R13), and Fluoromethane (R41). Only traces (equivalent to 0.8–1.2 mol % of pentafluoropropanol) of carbon were formed and deposited on the catalyst surface.

Activated carbon as a support shows superior activity than Alumina (Table 1, # 6–7). Among the three transition metals used, Ni is proven to be the most selective catalyst for this reaction (Table 1, #1, 6–7, and 10). A temperature of 450–500° C. is suitable for this reaction, a further increase in temperature results in low selectivity and high loss of starting material to byproducts (Table 1, # 1 and 4–5). The reactor pressure is kept at 1.2 psig during the reaction. An increase in pressure up to 10 psig decreases the selectivity drastically (Table 1, # 7–9).

The contact time was optimized at 23–25 sec. $N_2$, though, is used as a diluents to keep a constant contact time, can be eliminated by choosing a proper ratio of the two reactants. Lower selectivity (44%) was obtained when no $N_2$ is used in a similar reaction as in #1 (Table 1, #2). However, to minimize separation cost, $N_2$ is avoided by increasing the flow rate of $CH_4$ and Pentafluoropropanol. Almost similar results are obtained in the absence of $N_2$ when the same contact time was maintained by choosing proper flow rates of methane and pentafluoropropanol (Table 1, # 3).

TABLE 1

(Catalytic dehydration of pentafluoropropanol in the presence of methane[a])

| # | Catalyst | Temp °C. | $CH_4$, sccm | $N_2$, sccm | Pentafluoro-propanol, sccm | Conv. of alcohol[b] | Sel. to 1234yf[c] |
|---|---|---|---|---|---|---|---|
| 1 | Ni-mesh | 497 | 19 | 51 | 21 | 60 | 58 |
| 2 | Ni-mesh | 497 | 19 | 0 | 21 | 65 | 44 |
| 3 | Ni-mesh | 497 | 45 | 0 | 45 | 63 | 57 |
| 4 | Ni-mesh | 550 | 19 | 52 | 22 | 90 | 46 |
| 5 | Ni-mesh | 579 | 41 | 53 | 20 | 98 | 34 |
| 6 | Pd/Alumina | 452 | 25 | 52 | 21 | 87 | 33 |
| 7 | Pd/C | 452 | 25 | 51 | 20 | 92 | 55 |
| 8[d] | Pd/C | 452 | 25 | 51 | 20 | 96 | 41 |
| 9[e] | Pd/C | 452 | 25 | 51 | 20 | 100 | 29 |
| 10 | Pt/C | 450 | 25 | 50 | 20 | 83 | 46 |

[a]Reaction conditions: pressure, 1.2 psig; catalyst, 100 cc;
[b]mass flow controllers are used for flow measurement; conversion is the ratio of moles of pentafluoropropanol reacted to the total moles taken initially;
[c]selectivity is the ratio of moles of pentafluoropropanol converted to pentafluoropropene to moles of pentafluoropropanol reacted.
[d]pressure 5 psig;
[e]pressure 10 psig While we have shown and described several embodiments in accordance with our invention, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A process for producing a hydrofluoroalkene product which comprises:

mixing a dehydrating agent with a hydrofluoroalkanol, thereby forming a gaseous mixture; and contacting a catalyst with said gaseous mixture, thereby forming said hydrofluoroalkene product.

2. The process according to claim 1, wherein said hydrofluoroalkanol has the general formula:

$$RCH_2OH$$

wherein R is selected from the group consisting of: $CF_3$, $CF_3CF_2$, $CF_3CF_2CF_2$, and $CF_3CF_2CF_2CF_2$.

3. The process according to claim 2, wherein said hydrofluoroalkanol is pentafluoropropanol.

4. The process according to claim 3, wherein said pentafluoropropanol is 2,2,3,3,3-pentafluoro-1-propanol.

5. The process according to claim 1, wherein said catalyst is a transition metal.

6. The process according to claim 5, wherein said transition metal is at least one metal selected from the group consisting of: Ni, Pd, and Pt.

7. The process according to claim 1, wherein said catalyst is a supported catalyst.

8. The process according to claim 7, wherein said supported catalyst comprises a transition metal and a support material.

9. The process according to claim 8, wherein said support material is at least one selected from the group consisting of: activated carbon and γ-alumina.

10. The process according to claim 1, wherein said dehydrating agent is at least one gas selected from the group consisting of: methane, ethane, propane, butane, natural gas, alcohols, aldehydes and carbon monoxide.

11. The process according to claim 1, wherein said mixing step takes place at a temperature in the range between about 65 to about 80° C.

12. The process according to claim 1, further comprising preheating said gaseous mixture prior to said contacting step.

13. The process according to claim 12, wherein said preheating takes place at a temperature in the range between about 250 to about 450° C.

14. The process according to claim 1, wherein said contacting step takes place at a temperature in the range between about 400 to about 700° C.

15. The process according to claim 1, wherein said contacting step takes place of between about 20 to about 25 seconds.

16. The process according to claim 1, further comprising the step of neutralizing any residual HF contained in said hydrofluoroalkene product.

17. The process according to claim 16, wherein said HF is neutralized by passing said hydrofluoroalkene product through a KOH solution.

18. The process according to claim 1, wherein said hydrofluoroalkene product comprises at least one hydrofluoroalkene selected from the group consisting of compounds represented by the formula:

$$R_fCF=CH_2$$

wherein $R^f$ is selected from the group consisting of: $CF_3$, $CF_3CF_2$, and $CF_3CF_2CF_2$.

19. The process according to claim 18, wherein said hydrofluoroalkene is 2,3,3,3-tetrafluoro-1-propene.

20. The process according to claim 1, wherein said gaseous mixture further comprises at least one diluent selected from the group consisting of: nitrogen, helium, and argon.

21. The process according to claim 1, wherein the conversion of said hydrofluoroalkanol to hydrofluoroalkene is in the range between about 50 to about 100%.

22. The process according to claim 1, wherein the selectivity of hydrofluoroalkanol to hydrofluoroalkene is in the range between about 29 to about 100%.

23. The process according to claim 1, wherein the pressure during said contacting step is in the range between about 1 to about 100 psig.

* * * * *